United States Patent [19]

Yoshikumi et al.

[11] 4,380,536
[45] Apr. 19, 1983

[54] PHARMACEUTICAL COMPOSITION CONTAINING PARA-AMINO-BENZOIC ACID-N-D-MANNOSIDE AS AN ACTIVE INGREDIENT

[75] Inventors: Chikao Yoshikumi, Kunitachi; Yoshio Ohmura, Funabashi; Fumio Hirose, Tokyo; Masanori Ikuzawa, Tachikawa; Kenichi Matsunaga, Tokyo; Takayoshi Fujii, Tokyo; Minoru Ohhara, Tokyo; Takao Ando, Tokyo, all of Japan

[73] Assignee: Kureha Kagaku Kogyo Kabushiki Kaisha, Tokyo, Japan

[21] Appl. No.: 175,827

[22] Filed: Aug. 5, 1980

Related U.S. Application Data

[63] Continuation-in-part of Ser. No. 81,190, Oct. 2, 1979, Pat. No. 4,322,409, which is a continuation-in-part of Ser. No. 24,095, Mar. 26, 1979, abandoned.

[51] Int. Cl.$^3$ .............................................. A61K 31/70
[52] U.S. Cl. ...................................... 424/180; 536/22

[58] Field of Search ..................... 424/180; 536/18, 22

[56] References Cited

U.S. PATENT DOCUMENTS 2,659,689 11/1953 Schreiber .............................. 536/18

FOREIGN PATENT DOCUMENTS 2627076 5/1977 Fed. Rep. of Germany .

OTHER PUBLICATIONS

Chemotherapie von Tumoren, Weinheim, (1975), pp. 126–127.
Chemical Abstract, vol. 69, No. 1, (1968), 10628Z, p. 1022.
Chemical Abstract, vol. 48, 2001c, 2003a, 2003e, 1954.

Primary Examiner—Blondel Hazel
Attorney, Agent, or Firm—Wegner & Bretschneider

[57] ABSTRACT

Disclosed is a pharmaceutical composition containing p-aminobenzoic acid-N-D-mannoside or a pharmaceutically acceptable salt thereof as an active ingredient.

3 Claims, 2 Drawing Figures

PHARMACEUTICAL COMPOSITION CONTAINING PARA-AMINO-BENZOIC ACID-N-D-MANNOSIDE AS AN ACTIVE INGREDIENT

CROSS-REFERENCES TO RELATED APPLICATION

This application is a continuation-in-part of our co-pending application, Ser. No. 81,190 filed Oct. 2, 1979 U.S. Pat. No. 4,322,409, which is in turn a continuation-in-part of Ser. No. 24,095 filed Mar. 26, 1979 now abandoned.

BACKGROUND OF THE INVENTION

The present invention relates to a pharmaceutical composition containing a compound represented by the following general formula:

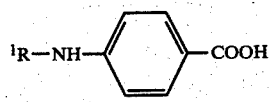

(1)

wherein $^1R$ denotes the residual group formed by removing the OH group of 1 position from mannose, or its pharmaceutically acceptable salt selected from the group consisting of its Na, K, Mg, Ca and Al salts.

The inventors of the present invention, during the course of searching chemical compounds having antitumor activity, have found that chemical compounds represented by the abovementioned formula (1) have a number of physiological activities such as blood sugar-reducing activity, antihypertensive activity, blood lipid-reducing activity, antiinflammatory activity and central nerve-depressing activity in addition to its antitumor activity.

Although the above-mentioned aminobenzoic acid derivatives are known compounds, no report has been found on the physiological activity of the compounds.

"Inoue, et al. N-Glycosides. XIX. Preparation of anthranilic acid N-glycosides., Chemical Abstracts, Vol. 48 (1954), Column 2001 i." and "Inoue, et al. N-Glycosides. XXV. Paper chromatography of N-glycosides., Chemical Abstracts, Vol. 48 (1954), Column 2003 a." disclose the chemical syntheses of the compounds which are the active ingredients of the pharmaceutical composition of the present invention. However, there is no utility disclosed in this prior arts and no teaching of pharmaceutical "dosage unit forms".

Furthermore, although U.S. Pat. No. 2,659,689 discloses a p-aldimino benzoic ester and a composition for protecting the human skin from erythema producing rals, the composition comprising a solution of p-aldimino benzoic ester, there is no teaching of pharmaceutical "dosage unit forms".

SUMMARY OF THE INVENTION

In an aspect of the invention, there is provided a pharmaceutical composition having effectiveness in antitumor activity, blood sugar-reducing activity, antihypertensive activity, blood lipd-reducing activity, antiinflammatory activity and central nerve-depressing activity, based on the discovery of the new medical use of the chemical compounds represented by the following formula (1).

BRIEF DESCRIPTION OF THE DRAWING

The annexed

DETAILED DESCRIPTION OF THE INVENTION

The active ingredient of the pharmaceutical composition of the present invention is a compound represented by the following formula:

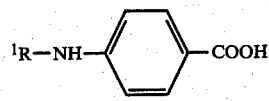

wherein $^1R$ is as described above, or its pharmaceutically acceptable salt selected from the group consisting of its Na, K, Mg, Ca and Al salts. The sugar moiety of the active ingredient has a structure of a six membered heterocyclic ring.

The method of preparation of the active ingredient of the present invention is illustrated as follows:

A mixture of 4.5 to 5 g of p-aminobenzoic acid, 5–6 g of D-mannose and 0.1 to 0.5 g of ammonium chloride was heated in 40 to 90 ml of 95 to 100% ethanol or pure methanol under a reflux condenser to induce condensation. After the reaction is over, the reactant is left at room temperature or in a cool place and the crystals separated out are collected by filtering the reactant solution. These crystals are washed with water, ethanol or ethyl ether, and then recrystallized from an aqueous solution of methanol or ethanol.

In order to substitute the hydrogen atom of the carboxyl group of the thus prepared compound with a base, it is preferable to follow the known method. The compound, para-aminobenzoic acid-N-D-mannoside, is dissolved in an aqueous ethanolic solution and an inorganic salt is added to the solution to effect the substitution.

Figure 1:
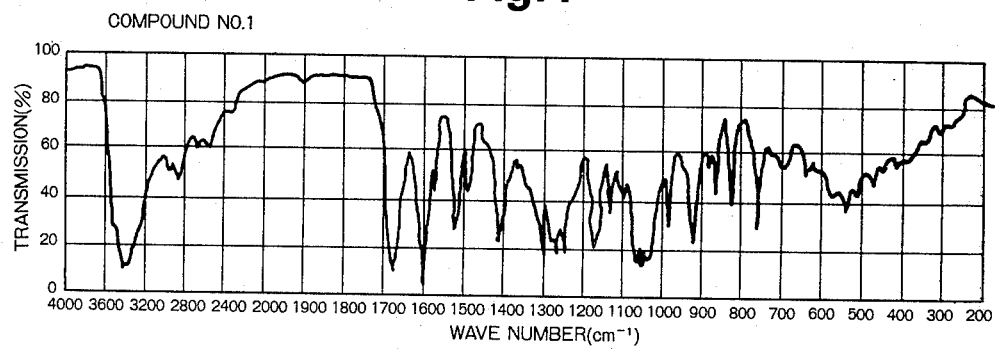
FIGS. 1 to 2 show respectively the infrared absorption spectra of respective compound No. 1 to No. 2 in Table 1.
Figure 2:
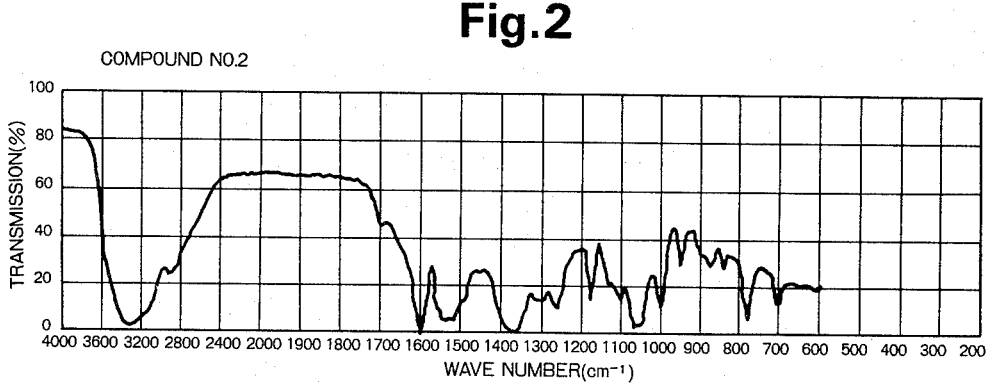

The physical properties of the compounds (the active ingredient of the pharmaceutical composition of the present invention) prepared by the above-mentioned methods are shown in Table 1, and their infrared absorption spectra are respectively shown in FIGS. 1 to 2. Methods of determination of the physical properties are as follows.

TABLE 1

| | Physical Properties of the Active Ingredients | | | |
|---|---|---|---|---|
| Compound | Melting point (°C.) | Specific rotation $[\alpha]_D^{20}$ | Elementary analysis (%) C:H:N | Ultraviolet absorption Maximum (millimicron) |
| 1. p-Aminobenzoic acid-N—D-mannoside | 182 (decomp.) | +35.7 in 94% ethanol | 52.0:5.7:4.7 (52.5:5.7:4.7) | 290 |
| 2. Sodium p-aminobenzoate-N— | 185–196 | −2 | 46.1:5.5:4.0 | 274 |

TABLE 1-continued

| | Physical Properties of the Active Ingredients | | | |
|---|---|---|---|---|
| Compound | Melting point (°C.) | Specific rotation $[\alpha]_D^{20}$ | Elementary analysis (%) C:H:N | Ultraviolet absorption Maximum (millimicron) |
| D-mannoside | (decomp.) | in water | (46.0:5.3:4.1) | |

Note:
(C:H:N): theoretical values of C, H and N (%).

(1) Melting point: determined by the use of micro melting point determination apparatus made by Yanagimotor Works, Japan.

(2) Specific rotation: determined by using direct-reading polarimeter Model OR-50 made by Yanagimoto Works, Japan, with a thickness of 50 mm of an aqueous ethanolic solution of the acidic active ingredient and an aqueous solution of the sodium salt of the acidic active ingredient.

(3) Molecular composition: Elementary analysis was carried out by using OHN-Coder Model MT-2 made by Yanagimoto Works, Japan.

(4) Ultraviolet absorption spectrum: by using self-recording spectrophotometer Model PS-3T made by Hitachi Works, Japan, on an aqueous ethanolic solution of the acidic active ingredient and on an aqueous solution of the sodium salt of the acidic active ingredient of the medicine.

(5) Infrared absorption spectrum: determined by KRr-method using infrared absorption spectrometer Model DS-701G made by Nippon Bunko Co., Ltd., Japan. The chart number of the spectrogram coincides with the number of specimens of the active ingredient of the pharmaceutical composition.

The followings are the physiological properties of the active ingredient of the pharmaceutical composition of the present invention described in the order of (1) acute toxicity, (2) antimicrobial activity, (3) mutagenicity, (4) delayed-type intracutaneous reaction and (5) antibody-producing activity.

(1) Acute toxicity

Acute toxicity of the active ingredient was examined by respective intraperitoneal and oral (forcible) administration to ICR-JCL mice. The specimen was dissolved in the physiological saline solution in intraperitoneal administration, and dissolved in distilled water in oral administration.

Their symptoms were observed after administration until the 7th day of administration, and LD$_{50}$ of the specimen was obtained from the mortality accumulated to the 7th day, according to the graphic method of Litchfield-Wilcoxon. The results are shown in Table 2. As is seen in Table 2, all of the active ingredients are qualified to be highly safe active ingredients of the pharmaceutical composition.

TABLE 2

| | Acute toxicity of the active ingredients (LD$_{50}$ in g/kg) | |
|---|---|---|
| Compound | Route of administration intraperitoneal | oral |
| Sodium p-aminobenzoate-N—D-mannoside | >10.00 | >10.00 |

(2) Antimicrobial activity

The active ingredient was dissolved in distilled water at a series of two fold dilution system. These diluted solutions were mixed with agar medium in 9 times by volume, and the mixture was poured into a petri dish. Heart infusion agar medium was used for bacteria, and Sabouraud's agar medium was used for fungi. After streaking with the pre-culture, the inoculated plates were incubated at 37° C. for 20 to 24 hours for bacteria and at 25° C. for 3 to 7 days for fungi, and then the growth was examined. The following microorganisms were used for assessing the antimicrobial activity:

Pseudomonas aeruginosa IAM 1514
Escherchia coli IFO 12734
Staphylococcus aureus 209 P
Bacillus subtilis IAM 1069
Saccharomyces cerevisiae IAM 4207
Candida albicans ATCC 752
Trichophyton mentagrophytes IFO 6124
Aspergillus niger IAM 3001

As the result of the above-mentioned tests, it was found that none of the tested active ingredients showed growth inhibition of all the microorganisms at a concentration of 1 mg/ml.

(3) Mutagenicity

As the first stage, the active ingredients were tested by rec-assay (i), and as the second stage, they were tested by reversion assay (ii).

(i) A strain of Bacillus subtilis M 45, a defectant of recombination repair, and another strain of Bacillus subtilis H 17 keeping recombination repair activity were inoculated to make thin own streaks not crossed at the start on B-2 agar culture plate (made by dissolving 10 g of meat extract, 10 g of polypeptone, 5 g of sodium chloride and 15 g of agar in 1000 ml of distilled water at a pH of 7.0).

Then, a circular sheet of filter paper 8 mm in diameter, which absorbed 0.04 ml of an aqueous solution of the active ingredient (using sterilized water) was put on the surface of the agar plate so as to cover the starting point of the above-mentioned streaks of bacterial culture. The inoculated B-2 agar culture was kept at 37° C. for a night and the length of growth-inhibited region was measured. Kanamycin was used as the negative control and Mitomycin C was used as the positive control. The results of the rec-assay are shown in Table 3.

(ii) The strains TA 98 and TA 100 (both are histidine requiring) of Salmonella typhimurium were used in the reversion assay.

Into 2 ml of a soft agar culture medium (the medium itself contains 6 g of sodium chloride and 6 g of agar in 1000 ml of distilled water) to which one tenth by volume of an aqueous solution of 0.5 mM of biotin and 0.5 mM of histidine, 0.1 ml of the bacterial suspension and 0.1 ml of an aqueous solution of the active ingredient were admixed and the mixture was layered on the minimum agar culture medium. After 2 days of incubation at 37° C., the number of revertant colonies was counted.

Furylfuramide (AF-2) was used as the positive control. The results of the reversion assay are shown in Table 4.

As is seen in Table 3, the active ingredients showed no mutagenicity even at a high concentration of 5000 microgram/disk. And as is seen in Table 4, the rate of occurrence of mutation by the active ingredient of the pharmaceutical composition of the present invention did not show any difference from that in the control to which no substance was added, even at a high concentration of 5000 microgram/plate. These findings demonstrate that the active ingredient is safe in view of mutagenicity.

TABLE 3

| | Result of rec-assay | | | |
|---|---|---|---|---|
| | | Length of growth-inhibition zone | | |
| Compound | Concentration (µg/plate) | M 45 (mm) | H 17 (mm) | *difference (mm) |
| Sodium p-aminobenzoate-N—D-mannoside | 500 | 0 | 0 | 0 |
| | 5000 | 0 | 0 | 0 |
| Kanamycin | 10 | 5 | 4 | 1 |
| Mitomycin C | 0.05 | 12 | 2 | 10 |

Note:
*difference = length of inhibition zone of M 45 minus length of inhibition zone of H 17

TABLE 4

| | Results of Reversion assay Test | | |
|---|---|---|---|
| | Concentration | Number of revertant colonies (n/plate) | |
| Compound | (µg/plate) | TA 100 | TA 98 |
| Sodium p-aminobenzoate-N—D-mannoside | 5000 | 138 | 5 |
| Furylfuramide | 0.1 | 911 | 167 |
| Control (nothing added) | — | 149 | 13 |

(4) Delayed-type intracutaneous reaction

In order to know the effects of the active ingredients on cellular immunity, the foot pad reaction test was carried out using ICR-JCL mice as experimental animals and erythrocytes of sheep as an antigen.

A mouse was primary-sensitized by injecting 0.2 ml of 10% suspension of sheep erythrocytes in physiological saline solution from the caudal vein and after 7 days of the first sensitization, 0.05 ml of 40% suspension of sheep's erythrocytes in physiological saline solution was injected in the foot pad for the second sensitization. The thickness of the foot pad was determined on the next day. The adminstration of the antive ingredient of the pharmaceutical composition of the present invention was carried out at the dousage of 250 mg/kg/day once a day for consecutive 5 days centering around the day when the first sensitization was carried out.

As the result, the increment of the thickness of the foot pad of the mouse administered with the active ingredient showed no significant difference as compared to the increment in the group of mouse not administered with the active ingredient.

(5) Antibody-producing activity

In order to know the effects of the active ingredients on humoral immunity, the hemagglutination test was carried out using ICR-JCL mice sensitized with sheep erythrocytes.

A mouse was sensitized by injecting 0.2 ml of 10% suspension of sheep erythrocytes in physiological saline solution from the caudal vein and after 7 days of sensitization the mouse blood was sampled for the hemagglutination test of determination of the antibody-producing activity. The active ingredient was administered for consecutive 5 days centering around the day of sensitization, intraperitoneally at the dosage of 250 mg/kg/day.

As the result, there was no significant difference in agglutination titer between the group administered with the active ingredient and the control group.

The followings are the pharmacological properties of the active ingredients of the pharmaceutical composition of the present invention described in the order of (1) blood sugar-reducing activity, (2) antihypertensive activity, (3) antitumour activity, (4) analgetic activity, (5) antipyretic activity, (6) antiinflammatory activity, and (7) blood lipid reducing activity.

(1) Blood sugar reducing activity

Streptozotocin was administered intraperitoneally to a group of Wistar rats at a dosage of 60 mg/kg and after confirming the positivity of urinary sugar of the animals on the 8th day, regular insulin was further administered to the rats to reduce both the uninary sugar and the blood sugar. Out of thus treated animals, those which certainly showed a higher urinary sugar value and also a higher blood sugar value (mean value of 500 mg/dl) after a few days of insulin-administration were used as the model animals suffering from artificial diabetes mellitus. The active ingredient was administered to the model animals orally as a solution in distilled water at the respective dosages of 30 and 300 mg/kg. Blood specimens were collected after 3 and 6 hours of the administration, and the determination of glucose in the specimen was carried out by using a RaBA- kit (made by Chugai Pharmaceutical Co., Japan) according to the enzyme method.

The results are shown in Table 5. As is seen in Table 5, the difference between the values of blood sugar before and after the administration of every active ingredient (Δ value) was larger than the Δ value of control which were given only distilled water.

TABLE 5

| | Blood sugar-reducing activity | | |
|---|---|---|---|
| | | Change (Δ value, mg/dl) of blood sugar after | |
| Compound | Dose (mg/kg) | 3 hr. | 6 hr. |
| Sodium p-aminobenzoate-N—D-mannoside | 30 | −160 | −118 |
| | 300 | −190 | −146 |
| Control | — | −36 | −39 |

(2) Antihypertensive activity

An aqueous solution of the active ingredient in distilled water was orally administered to rats of spontaneous hypertension at respective dosages of 30 and 300 mg/kg and their blood pressure was determined after 3 and 6 hours of administration by a sphygmomanometer (made by Ueda Works, Japan, Model USM-105R). The difference of blood pressures before and after the administration was used to evaluate the antihypertensive activity of the active ingredients. Mean value of blood pressure of the above-mentioned rats in spontaneous hypertension was 200 mmHg.

The results are shown in Table 6. As is seen in Table 6, all the tested active ingredients clearly showed the antihypertensive effect.

TABLE 5

| Antihypertensive Activity | | | |
|---|---|---|---|
| | | Reduced amount of blood pressure after | |
| Compound | Dose rate (mg/kg) | 3 hr. (mm Hg) | 6 hr. (mm Hg) |
| Sodium p-aminobenzoate-N—D-mannoside | 30 300 | 16 18 | 20 22 |
| Control | — | −2* | 2 |

Note:
*Blood pressure was raised by 2 mmHg.

(3) Antitumour activity

Sarcoma 180 were transplanted subcutaneously into the right axiallary of ICR-JCL mice at the rate of $1 \times 10^6$ cells/mouse, and from after 24 hours of transplantation an aqueous solution of the active ingredient in sterilized physiological saline solution was orally administered every other day at a dose rate of 500 mg/kg, 10 times in all. On the 25th day of the transplantation, the nodular tumour(s) was extirpated and weighed.

The inhibition ratio (I.R.) (%) of the active ingredient was calculated by the following formula:

$$(1 - T/C) \times 100 = \text{I.R. (\%)}$$

wherein
T: mean weight of the tumour(s) in treated group of mice
C: mean weight of the tumour(s) in control group* of mice
Note: *mice transplanted, but not administered.

The results of the test are shown in Table 7. As is seen in Table 7, all the active ingredients tested exhibited an antitumour activity.

TABLE 7

| Antitumourigenic activity against Sarcoma-180 | |
|---|---|
| Compound | Inhibition ratio (I.R. %) |
| Sodium p-aminobenzoate-N—D-mannoside | 29.0 |

Note:
Amount of administration was 10 × 500 mg/kg p.o.

(4) Analgetic Activity

Determination by the mechanical stimulation method (by applying pressure)

Female ICR mice which showed a threshold value of pain of 50 to 80 mmHg when their tail base part was pressed by a pressure stimulation apparatus (made by Natsume Works, Japan) of Takagi and Kameyama were chosen as test animals, ten animals comprising a group.

After administering the active ingredient, the test was carried out as the time passes and the applied pressure and the time period until the animal showed a quasi-escaping reaction were determined to evaluate the analgetic activity of the active ingredient.

The results are shown in Table 8. As is seen in Table 8, the pressure applied on animals when the animal showed the quasiescaping reaction was higher in animals to which the active ingredient has been applied than in animals not administered, and the time period from the beginning to the time point when the animal showed the reaction was longer in animals administered with the active ingredient than in animals not administered. Thus, the analgetic activity of the active ingredient was confirmed.

Determination by the chemical stimulation method

The active ingredient was orally administered to a group (ten animals) of female ICR mice of age of 5 to 6 weeks, and after 30 min of the administration an aqueous 0.6% acetic acid solution was intraperitoneally injected into the mouse at a dose rate of 0.1 ml/10 g of body weight. The number of writhing motion which occurred in the mouse during 10 minutes after 10 minutes of intraperitoneal administration was recorded. The analogetic activity was evaluated from the writhing syndrome inhibiting ratio obtained by the following formula:

$(1 - T/C) \times 100 = $ writhing syndrome inhibiting ratio (%) wherein
T: Mean number of writhing syndrome in the group administered
C: mean number of writhing syndrome in the control group.

The results are shown in Table 9. As is seen in Table 9, every active ingredient of the pharmaceutical composition of the present invention showed analgetic activity. The above-mentioned process was carried out following the method of Kostet et al. (1959)

TABLE 8

| Analgetic activity by the mechanical stimulation method | | |
|---|---|---|
| | Quasi-escope reaction pressure at time until occurrence | |
| Compound | (mmHg) | (sec.) |
| Sodium p-aminobenzoate-N—D-mannoside | 95 | 39 |
| Control | 70 | 33 |

Note:
Amount of administration, 1000 mg/kg p.o.

TABLE 9

| Analgetic activity by the chemical stimulation method | |
|---|---|
| Compound | I.R. (%) |
| Sodium p-aminobenzoate-N—D-mannoside | 71.2 |

Note:
Amount of administration was 1000 mg/kg p.o.

(5) Antipyretic activity

Following the method of Winter et al. (1961), a 20% suspension of beer yeast was subcutaneously injected to a group (consisting of 6 animals) of rats, and after 10 hours of fasting, the active ingredient was orally administered to the rats and their rectal temperature was determined.

The antipyretic activity is expressed by the ratio of inhibiting pyrexia due to beer yeast (I.R. %) at the time when the antipyretic activity of the active ingredient is at its maximum according to the following formula:

$$\text{Antipyretic activity} = \text{I.R. (\%)} = \frac{C_1 - T}{C_1 - C_2} \times 100$$

wherein

T: mean rectal temperature of rats to which the active ingredient was administered.

C$_1$: mean rectal temperature of rats injected beer yeast, without the active ingredient.

C$_2$: mean rectal temperature of untreated rats (control)

The results are shown in Table 10. As is seen in Table 10, all the active ingredients exhibited a considerable antipyretic activity.

TABLE 10

| | Antipyretic activity |
|---|---|
| Compound | Antipyretic activity (suppressing pyrexia) I.R. (%) |
| Sodium p-aminobenzoate-N—D-mannoside | 20.5 |

(6) Antiinflammatory activity

(a) Carrageenin-edema inhibitory activity

Following the method of Van Arman et al. (1963), the active ingredient was forcibly and orally administered to each rat of a group consisting of 10 animals at the dose rate of 1000 mg/kg, and after one hour of the administration 0.1 ml of 1% suspension of carrageenin in physiological saline solution was injected to their right foot pad. The volume of the foot pad was determined as time passes and the antiinflammatory activity was expressed by the ratio of inhibition of the swelling of the foot pad due to carrageenin by the active ingredient, using the maximum determined value during 1 to 4 hours after the injection, and calculating by the following formula:

$(1 - T/C) \times 100 = I.R.(\%) =$ antiinflammatory activity wherein

T: mean value of volumes of planta in administered animals

C: mean value of volume of the foot pad of control (not administered and then injected)

The results are shown in Table 11. As is seen in Table 11, all the ingredients tested showed the inhibitory activity against the edema caused by carrageenin.

(b) Antigranuloma activity

Following the method of Winter et al. (1963), two cotton wool pellets were implanted into the skin of back of each rat of a group consisting of 6 rats at the symmetrical positions having the median line as the axis of symmetry, the weight of one pellet being 30±1 mg. Oral administration of 1000 mg/kg/day of the active ingredient was carried out for consecutive 7 days. On the 8th day, the granuloma formed in the rats was extirpated and weighed after drying. The antigranuloma activity expressed by the ratio of inhibition of the growth of the granuloma (I.R.%) was calculated in a manner as shown in (6) (a), and the results are shown in Table 11. As is seen in Table 11, each active ingredient exhibited the inhibiting activity of growth of the granuloma.

(c) Antiexudation activity

Following the method of Baris et al. (1965), a volume of air was injected subcutaneously in the back of each rat of a group consisting of 6 rats to make a air pouch, and then 0.5 ml of 1% croton oil solution is sesame oil was injected into the pouch. The oral administration of 1000 mg/kg/day of the active ingredient was then began to continue for 5 days. On the 6th day, the amount of exsudated liquid into the puch was determined and the anti exsudation activity expressed by the ratio of inhibitory activity to exudation was calculated in a manner as shown in (6)(a). The results are shown in Table 11. As is seen in Table 11, all the active ingredient tested exhibited the anti-exsudation activity.

(d) Antiadjuvant-arthritis activity

Following the method of Fujiwara et al. (1971), *Mycrobacterium tuberculosis* suspended in liquid paraffin was injected subcutaneously into the right foot pad of each rat of a group consisting of 6 rats. After 14 days of the injection, rats with similar volume of the foot pad were chosen to form groups (10 animals/group), each active ingredient was orally administered daily from the 15th day for consecutive 7 days at the dose rate of 1000 mg/kg/day. The volume of the foot pad of rats was determined, and the antiadjuvant arthritis activity of each active ingredient was calculated as the ratio of inhibiting the swelling of the foot pad by using the formula shown in (6) (a). The results are shown in Table 11. As is seen in Table 11, all the tested active ingredient exhibited the antiadjuvant arthritis activity.

TABLE 11

| | Antiinflammatory activity | | | |
|---|---|---|---|---|
| Compound | *edema | *granuloma | *exudation | *arthritis |
| Sodium p-aminobenzoate-N—D-mannoside | 3.8 | 29.9 | 5.0 | 30.5 |

Note:
Amount of administration of the active ingredient = 1000 mg/kg/day

(7) Blood lipid reducing activity

Japanese male white rabbits were fed for about 3 months with solid feed (CR-1) containing 1% of cholesterol and those animals in which the increase of seral lipid component was confirmed were used as the model animals having experimental arteriosclerosis.

An aqueous solution of the active ingredient in distilled water was administered respectively at the dose rates of 30 and 300 mg/kg orally and after the administration, blood specimen was collected as time passes from the auricular vein and the change of total cholesterol (determined by the enzyme method), phospholipid (determined by the enzyme method) and beta-lipoprotein (determined by turbidmetry) in the serum was observed.

The results are shown in Table 12. In Table 12, the values of serum cholesterol (mean value of 550 mg/dl), of serum phospholipid (mean value of 320 mg/dl) and of serum beta-lipoprotein (mean value of 2500 mg/kg) before administration were respectively subtracted from the respective values after 3 and 6 hours of the administration, and only the differences are shown, respectively. Therefore, the minus value shows the decrease and the plus value shows the increase of the respective values due to the administration. As is clearly seen in Table 12, every active ingredient exhibited an activity of reducing the lipid components of serum as compared to control.

TABLE 12

| Compound | Dose (mg/kg) | Activity of reducing blood lipids | | | | | |
|---|---|---|---|---|---|---|---|
| | | Phospholipid (mg/dl) | | beta-Lipoprotein (mg/dl) | | Cholesterol (mg/dl) | |
| | | 3 hr. | 6 hr. | 3 hr. | 6 hr. | 3 hr. | 6 hr. |
| Sodium p-aminobenzoate-N—D-mannoside | 30 | −37 | −43 | −133 | −142 | −190 | −80 |
| | 300 | −50 | −75 | −156 | −183 | −150 | −234 |
| Control | — | 0 | −19 | 0 | +3 | +8 | −4 |

Now, the formulation of the active ingredients to make the pharmaceutical composition of the present invention is described below.

In the case where the pharmaceutical composition is used as an antiinflammatory agent, it is able to use the pharmaceutical composition in the form which is convenient to obtain the effectiveness according to the kinds and the symptoms of the disease, and moreover, the active ingredient may be used as itself or may be used as mixtures combined with any diluent allowable in pharmaceutical process and with other medicines.

The pharmaceutical composition of the present invention is administered orally or parenterally and accordingly, the pharmaceutical composition of the present invention may take any form optionally for the oral or parental administration.

The pharmaceutical composition of the present invention may be offered as a form of unit administration. The form of the pharmaceutical composition of the present invention may be powder, granule, tablet, sugar-coated tablet, capsulated one, suppository, suspension, solution, emulsifiable concentrate, ampouled one, injection, etc. As a diluent, any one of solids, liquids and semisolids may be utilized, for instance, excipients, binders, wetting agents, disintegrating agents, surfactants, demulcents, dispersing agents, buffering agents, perfumes, preservatives, dissolution aids and solvents. Moreover, one or more than one of these adjuvants may be used in combination or in mixtures.

The pharmaceutical composition of the present invention may be formulated by any known method, and the amount of the active ingredient contained in the composition (preparation) is generally from 0.01% to 100% by weight.

The pharmaceutical composition of the present invention may be administered orally or parenterally to human or animals, however, it is preferably administered orally. Sublingual administration is included in oral administration. Parenteral administration includes subcutaneous-, intramuscular- and intravenous injection and the injection by drop method.

The dose of the pharmaceutical composition of the present invention depends upon the age, the personal difference and the state of disease, and whether the object is human or animal and accordingly, an extraordinal amount may be administered than the following dose: Generally, for human, the oral dose is 0.1–1000 mg/kg body weight/day, preferably 1–500 mg/kg/day and the parenteral dose is 0.01–200 mg/kg/day, preferably 0.1–100 mg/kg/day divided into 1–4 parts, one part being administered in one time.

The followings are the more detailed explanation of the formulation and the production of the pharmaceutical composition of the present invention in examples.

EXAMPLE 1

(Formulation)

10 parts by weight of one of the active ingredients of the present invention (Sodium p-aminobenzoate-N-D-mannoside), 15 parts by weight of (heavy) magnesium oxide and 75 parts by weight of lactose were uniformly mixed and formulated into powder or granules. The powder is filled in capsules to be capsulated formulation.

EXAMPLE 2

(Formulation)

45 parts by weight of one of the active ingredients of the present invention (Sodium p-aminobenzoate-N-D-mannoside), 15 parts by weight of starch, 16 parts by weight of lactose, 21 parts by weight of crystalline cellulose, 3 parts by weight of polyvinyl alcohol and 30 parts by weight of water were uniformely mixed, crushed and formulated, and then dried and shifted to be granules.

EXAMPLE 3

(Formulation)

94 parts by weight of one of the active ingredients of the present invention (sodium p-aminobenzoate-N-D-mannoside), 6 parts by weight of polyvinyl alcohol and 30 parts by weight of water were mixed and the mixture was processed as in Example 2 to be granules. To 90 parts by weight of the thus processed granules 10 parts by weight of crystal-line cellulose were mixed and the mixture was compression-formulated to be tablets 8 mm in diameter. The tablets were coated with syrup, gelatine and precipitated calcium carbonate to be coated tablets.

EXAMPLE 4

(Formulation)

0.6 parts by weight of one of the active ingredients of the present invention (sodium p-aminobenzoate-N-D-mannoside), 2.4 parts by weight of an non-ionic surfactant and 97 parts by weight of physiological saline solution were mixed under heating and then the mixture was sterilized to be an injection.

EXAMPLE 5

(Production of p-aminobenzoic acid-N-D-mannoside and its sodium salt)

A mixture of 2.0 g of p-aminobenzoic acid, 3.0 g of D-mannose and 0.2 g of ammonium chloride was heated in 10 ml of ethanol for about one hour under a reflux condenser. After the reaction was over, the reactant was left at room temperature to separate crystals. After filtering the reactant and washing the collected crystals with water, dilute ethanol and then with a small amount of ether, the crystals were recrystallized from 50% methanol to form colorless needles at the yield of 56.1%. Thus obtained p-aminobenzoic acid-N-D-mannoside was slowly dissolved in a solution forded by dissolving 2.5 mg of sodium hydroxide into 2.5 ml of water. After filtering the solution and condensing the filtrate, a large excess of acetone was added to the condensate to obtain crystals. After dehydrating and drying the crystals, they were recrystallized from a mixed solvent consisting of 5 parts by volume of water and 1 part by volume of acetone to obtain colorless crystals of sodium p-aminobenzoate-N-D-mannoside at a yield of 95%, total yield from p-aminobenzoic acid being 95%.

EXAMPLE 6

A case of essential hypertension

The patient was a man of 70 in age and was visiting the hospital on his hypertension as the chief disease. The present substance was internally administered 4 times daily at a rate of 800 mg (sodium p-aminobenzoate-N-D-mannoside)/day with a standard sign of evaluation of the reduction of blood pressure of 20 mmHg at contraction period and of 10 mmHg at dilatation period.

The blood pressure which was 195/95 mmHg (contraction/dilatation) before administration became 185/90 after 10 days of administration, 165/75 after 20 days of administration and 165/80 mmHg after 30 days of administration together with the improvements of cerebronerval complaints such as feeling heaviness in the head, feeling of dizziness and insomnia.

What is claimed is:

1. A pharmaceutical composition in dosage unit form, which comprises a dosage amount effective for the treatment of hypertension of a compound represented by the formula:

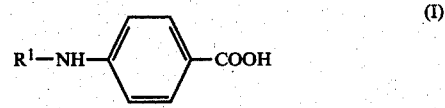

(I)

wherein $R^1$ denotes the residual group formed by removing from mannose the OH at the 1-position thereof, or a pharmaceutically acceptable salt thereof, and a carrier or diluent therefor.

2. A pharmaceutical composition according to claim 1, wherein said compound is p-aminobenzoic acid-N-D-mannoside.

3. A pharmaceutical composition according to claim 1, wherein said compound is sodium p-aminobenzoate-N-D-mannoside.

* * * * *

UNITED STATES PATENT AND TRADEMARK OFFICE
CERTIFICATE OF CORRECTION

PATENT NO. : 4,380,536
DATED : April 19, 1983
INVENTOR(S) : Chikao YOSHIKUMI et al.

It is certified that error appears in the above-identified patent and that said Letters Patent is hereby corrected as shown below:

On The Title Page:
In "Related U.S. Application Data", please change "Pat. No. 4,322,409" to --Pat. No. 4,322,408--.

Signed and Sealed this

Twentieth Day of December 1983

[SEAL]

Attest:

GERALD J. MOSSINGHOFF

Attesting Officer      Commissioner of Patents and Trademarks